United States Patent [19]

Böhner et al.

[11] 4,006,157
[45] Feb. 1, 1977

[54] PROCESS FOR THE PREPARATION OF 1,2,4-TRIAZOLE DERIVATIVES

[75] Inventors: Beat Böhner, Binningen; Dag Dawes, Pratteln; Hermann Kny, Fullinsdorf; Willy Meyer, Basel, all of Switzerland; Jean Perchais, Rixheim, France

[73] Assignee: Ciba-Geigy Corporation, Ardsley, N.Y.

[22] Filed: June 24, 1975

[21] Appl. No.: 589,991

Related U.S. Application Data

[63] Continuation-in-part of Ser. No. 460,624, Dec. 4, 1974, abandoned.

[30] Foreign Application Priority Data

Apr. 17, 1973 Switzerland .................... 5495/73

[52] U.S. Cl. .................... 260/308 R; 260/308 C
[51] Int. Cl.$^2$ .................................. C07D 249/12
[58] Field of Search .................... 260/308 R, 308 C

[56] References Cited

FOREIGN PATENTS OR APPLICATIONS 1,215,164  4/1966  Germany .................... 260/308 R
1,940,367  2/1971  Germany .................... 260/308 C

*Primary Examiner*—Alton D. Rollins
*Attorney, Agent, or Firm*—Harry Falber

[57] ABSTRACT

Preparation of 1-isopropyl-3-hydroxy-5-chloro-1,2,4-triazole by reacting isopropylhydrazine hydrochloride with N-chlorocarbonylisocyanidedichloride.

3 Claims, No Drawings

PROCESS FOR THE PREPARATION OF 1,2,4-TRIAZOLE DERIVATIVES

This application is a continuation-in-part application of Ser. No. 460,624, filed Dec. 4, 1974, now abandoned.

The present invention relates to a process for the preparation of 1-isopropyl-3-hydroxy-5-chloro-1,2,4-triazole. 1-Isopropyl-3-hydroxy-5-chloro-1,2,4-triazole is of particular importance as intermediate for the production of pest control agents, e.g. the 1,2,4-triazolyl phosphates and thiophosphates described in U.S. patent application Ser. No. 310,530 filed Nov. 29, 1972, now U.S. Pat. No. 3,867,396. The 1,2,4-triazolyl phos- The 1,2,4-triazolyl phosphates and thiophosphates which are obtainable by reacting 1-isopropyl-3-hydroxy-5-chloro-1,2,4-triazole with a dialkylphosphoric or dialkylthiophosphoric halide in particular possess insecticidal and acaricidal properties and may be used against all development stages, e.g. eggs, larvae, pupae, numphs and adults of insects and representatives of the order Acarina, as described in detail in U.S. Pat. No. 3,867,396.

It is known from Deutsch Auslegeschrift 1,215,164 to prepare 1,3,5-trisubstituted 1,2,4-triazoles of the formula

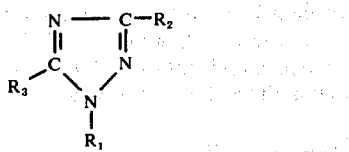

wherein $R_1$ represents an optionally substituted alkyl, cycloalkyl, aralkyl or aryl group and $R_2$ and $R_3$ represents chlorine atoms or perchlorinated alkyl groups, but one of the symbols $R_2$ and $R_3$ can also represent an optionally substituted aryl group, by reacting a monosubstituted hydrazine of the formula

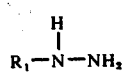

or a salt thereof at a temperature of from $-20°$ to $+200°$, optionally in a solvent and optionally in the presence of a base, with a polychloro-2-aza-propene of the formula

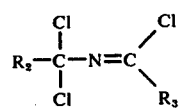

in which formulae, $R_1$, $R_2$ and $R_3$ have the meaning given above. In the case of $R_3$ being a chlorine atom this process also includes the formation of 1,3,5-trisubstituted 1,2,4-triazoles from isocyanide dichlorides and monosubstituted hydrazines. However, this process cannot be employed for the preparation of 1-isopropyl-3-hydroxy-5-chloro-1,2,4-triazole because it does not provide a possibility of introducing a hydroxy group in 3-position.

Further, it is known from Deutsche Offenlegungsschrift 1,940,367 to prepare 1,2,4-triazole derivatives of the formula

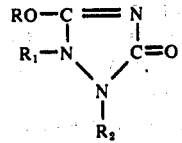

wherein R represents a halogenated alkyl group or an optionally substituted aromatic residue which can also be connected with heterocyclic groups, $R_1$ and/or $R_2$ stand for hydrogen, optionally substituted aliphatic, aromatic or heterocyclic residues, or one of the symbols $R_1$ and $R_2$ represents the grouping $R_3$—CO— or $R_3$—$SO_2$— in which $R_3$ stands for an aliphatic, aromatic or heterocyclic group, by reacting an iminocarbonic acid derivative of the formula

wherein R represents a halogenated alkyl group or an optionally substituted aromatic radical which can also be connected with heterocyclic groups, Y stands for halogen and X stands for halogen, an alkoxy or aryloxy group, at temperatures between $-30°$ to $+100°$ C, optionally in the presence of a diluting agent with a hydrazine derivative of the formula

wherein $R_1$ and $R_2$ have the meaning given above. As described in the Examples the process is carried out in the presence of excess hydrazine as acid binding agent. As it is further shown by the Examples 1,3-disubstituted 3-hydroxy-1,2,4-triazoles were only obtained from N-chlorcarbonyl iminocarbonic acid ester chlorides, i.e. from starting material of the above formula in which X and Y are chlorine atoms, when these starting materials were reacted with phenyl or phenylsulphonylhydrazines. When N-chlorocarbonyliminocarbonic acid ester chlorides were reacted with alkylhydrazines 1,3-disubstituted 5-hydroxy-1,2,4-triazoles are obtained (c.f. Example 5). On the other hand 1,5-disubstituted 3-hydroxy-1,2,4-triazoles were obtained when alkylhydrazines were reacted with N-phenoxycarbonyl iminocarbonic acid chlorides (c.f. Example 9).

It has now been found that 1-isopropyl-3-hydroxy-5-chloro-1,2,4-triazole can be prepared by reacting isopropylhydrazine hydrochloride with N-chlorocarbonylisocyanidedichloride of the formula

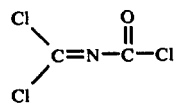

in the presence of a solvent.

Suitable solvents are, e.g. aliphatic and aromatic hydrocarbons or halogenated hydrocarbons, such as hexane, petroleum ether, chloroform, methylene chloride, halogenated ethanes, benzene, toluene, xylenes, ethers and ethereal compounds such as dialkyl ether, 1,2-dimethoxyethane, dioxane, tetrahydrofuran, N,N-dialkylated amides such as dimethylformamide, sulphoxides such as dimethylsulphoxide, nitriles such as acetonitrile, etc., or mixtures of such solvents with each other; for the cyclisation reaction, it is also possible to use water or hydrous solvents. Particularly suitable are also two-phase reaction media consisting of water and an organic solvent not miscible with water, such as chloroform, methylene chloride and toluene.

The process according to the invention is performed under normal pressure and in a temperature range of 0° to 80° C. The reactants are used in the process in equimolar amounts, whereby an excess of the one or the other reaction partner can contribute towards the completion of the reaction.

The process according to the invention is further illustrated by the following examples:

EXAMPLE 1

Preparation of 1-isopropyl-5-chloro-3-hydroxy-1,2,4-triazole 16.0 g of N-chlorocarbonylisocyanidedichloride is added dropwise at 20° C, with stirring, to 11.0 g of isopropylhydrazine-hydrochloride suspended in 100 ml of acetonitrile. The reaction proceeds exothermically and is controlled with an ice bath. The mixture is subsequently refluxed for 2 hours, with hydrochloric acid gas being released. On cooling to room temperature, there is precipitated a crystalline product; this is then filtered off, and dried in vacuo to yield an amount of 5.2 g. The mother liquor is concentrated in vacuo, and the residue boiled with 50 ml of water for 5 minutes. The precipitated product is again filtered off, and dried in vacuo to obtain an additional yield of 4 g of the compound of the formula

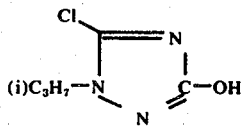

having a melting point of 101°–103° C.

EXAMPLE 2

A solution of 5.5 g (0.05 mole) of isopropylhydrazinehydrochloride in 80 ml of water is added dropwise, in the course of 2 hours, to a solution cooled to −5° C of 8.0 g (0.05 mole) of N-chlorocarbonylisocyanidedichloride in 20 ml of toluene, with the temperature being maintained between −5° C and −10° C. The whole is subsequently concentrated to dryness by evaporation, and the residue extracted with 50 ml of ethanol. The resulting ethanolic solution is again concentrated to dryness by evaporation, and the residue recrystallised from 20 ml of water to obtain 2.39 g of 1-isopropyl-3-hydroxy-5-chloro-1,2,4-triazole, M.P. 101°–102° C.

EXAMPLE 3

240 g (1.5 moles) of gaseous N-chlorocarbonylisocyanidedichloride is introduced, in the course of 10 hours, into a solution cooled to −10° C of 110.5 g (1 mole) of isopropylhydrazine-hydrochloride in 250 ml of water. After completion of the addition, the cooling bath is removed, and stirring maintained for a further 15 hours at room temperature. The residue obtained after concentration of the acid solution by evaporation to dryness is suspended in 150 ml of water; the pH-value of the suspension is adjusted to 4 by addition of sodium hydroxide solution, and the suspension then filtered: the resulting yield is 87.5 g of crude 1-isopropyl-3-hydroxy-5-chloro-1,2,4-triazole, M.P. 92°–98° C, which melts at 101°–103° C after recrystallisation from water.

What we claim is:

1. Process for the preparation of 1-isopropyl-3-hydroxy-5-chloro-1,2,4-triazole wherein isopropylhydrazine hydrochloride is reacted with N-chlorocarbonylisocyanide dichloride in approximately equimolar amounts in the presence of a polar solvent.

2. Process according to claim 1 wherein acetonitrile or water is used as polar solvent.

3. Process according to claim 1 which is carried out in a temperature range of 0° to 80° C.

* * * * *